United States Patent

Nordin

[11] Patent Number: 5,282,747
[45] Date of Patent: Feb. 1, 1994

[54] SUPERSTRUCTURE FOR AN ARTIFICIAL TOOTH

[76] Inventor: Harald E. Nordin, Villa Amphion, CH-1822 Chernex, Switzerland

[21] Appl. No.: 909,607

[22] Filed: Jul. 7, 1992

[30] Foreign Application Priority Data

Jul. 8, 1991 [EP] European Pat. Off. ........ 91810533.9

[51] Int. Cl.$^5$ ............................................. A61C 5/08
[52] U.S. Cl. ..................................... 433/221; 433/220
[58] Field of Search ........................ 433/219, 220, 221

[56] References Cited

U.S. PATENT DOCUMENTS

| | | | |
|---|---|---|---|
| 313,738 | 3/1885 | How | 433/221 |
| 468,922 | 2/1892 | Stanbough | 433/221 |
| 4,239,489 | 12/1980 | Ellman et al. | 433/220 |
| 4,427,383 | 1/1984 | Goldman | 433/220 |
| 5,085,586 | 2/1992 | Johnson | 433/224 |
| 5,094,620 | 3/1992 | Nordin | 433/220 |
| 5,118,294 | 6/1992 | Kurer | 433/220 |

FOREIGN PATENT DOCUMENTS

| | | |
|---|---|---|
| 0306429 | 8/1988 | European Pat. Off. . |
| 0408817 | 7/1989 | European Pat. Off. . |
| 745543 | 4/1940 | Fed. Rep. of Germany ...... 433/220 |
| 3316785 | 5/1983 | Fed. Rep. of Germany . |
| 721042 | 2/1932 | France ................................ 433/220 |
| 641947 | 6/1981 | Switzerland . |

*Primary Examiner*—John J. Wilson
*Assistant Examiner*—Cindy A. Cherichetti
*Attorney, Agent, or Firm*—Ostrolenk, Faber, Gerb & Soffen

[57] ABSTRACT

A superstructure for an artificial tooth is formed of a a root post which is screwed into a root canal of a tooth stump. The root post includes a cylindrical tap having a cutting thread, and is capable of guiding a sleeve-shaped rose cutter having a curved cutting surface to produce a tooth recess with a lower curved portion. The tooth recess is concentric with respect to the root post. A sleeve-shaped crown anchor is concentrically secured to the root post and has a lower curved portion which fits into and corresponds with the lower curved portion of the recess. The artificial tooth is secured on the crown anchor.

13 Claims, 1 Drawing Sheet

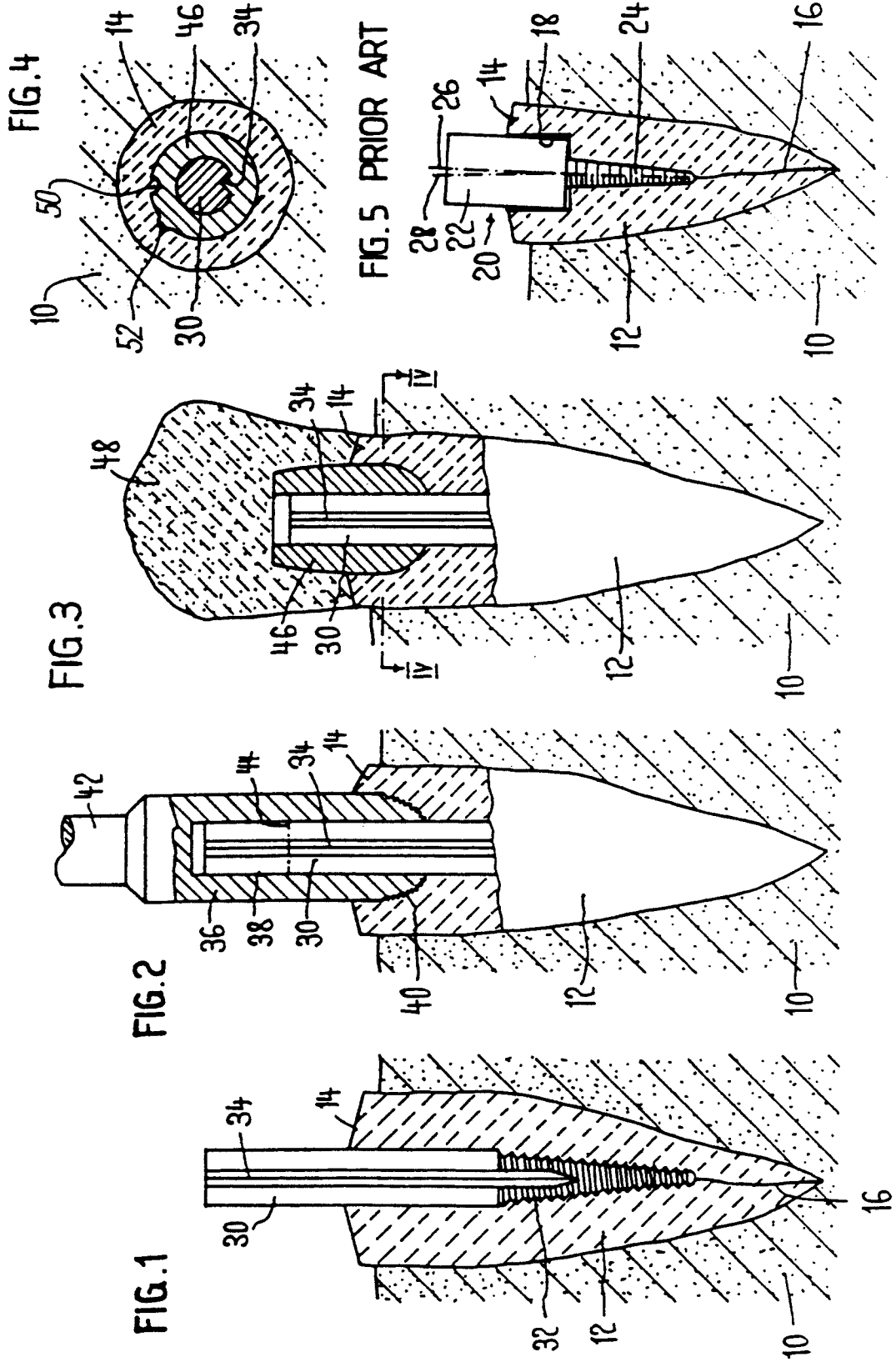

SUPERSTRUCTURE FOR AN ARTIFICIAL TOOTH

BACKGROUND OF THE INVENTION

1. Field of the Invention

The present invention relates to a superstructure for an artificial tooth, comprising a root post which is adapted to be screwed into the root canal of a tooth, and a crown anchor.

2. Description of the Prior Art

In a known manner, the general procedure for the construction of artificial teeth, where use can be made of an existing, healthy or repairable root and a stump protruding from the jaw, is shown in FIG. 5. The aforesaid figure represents the state of the art.

In order to produce an artificial tooth, first a tooth anchor inserted in the dentine is required which must form a solid connection with the existing tooth torso; otherwise, the crown will not be solidly connected to the tooth fragment.

FIG. 5 shows a lower jaw molar as an example of the prior art procedure.

Tooth fragment 12 is lodged in jaw bone 10, its upper portion 14 projecting above the upper edge of the jaw bone. Root canal 16 is now cleaned in a manner known per se and enlarged if necessary. In the upper area of tooth stump 12, an essentially cylindrical recess 18 is milled. The two mentioned operations may also be carried out in reverse order. A crown anchor 20 is inserted in the resulting cavity by means of a corresponding tool. The anchor is only roughly schematically shown in FIG. 5, but it is provided with a cylindrical body 22 whose external diameter corresponds to the internal diameter of recess 18 of the tooth and which is centrally and axially provided with a threaded pin 24; the pin 24 being intended to be screwed into the prepared root canal 16.

It may now happen, and it is indeed very often the case, that axis 26 of the prepared root canal, i.e. the axis that is defined as anchor 20 is screwed in, does not coincide with axis 28 of cylindrical recess 18, but rather forms an angle therewith. Since the diameters of recess 18 and of anchor 20 do not differ greatly, the described axial angle results in that the upper edge portion 14 of the tooth stump is broken off as anchor 20 is screwed into tooth 12, until it abuts to the bottom of said recess, as is directly apparent in FIG. 5.

SUMMARY OF THE INVENTION

The present invention aims to overcome the prior art adeficiencies by creating a superstructure which is free of breaking risks and does not damage the already unsolid tooth stump.

This task is solved by a superstructure for an artificial tooth wherein the root post is in the form of a cylindrical tap having a cutting thread and a groove extending axially along the external side of the post and serves as a guide for a sleeve-shaped rose cutter intended to produce a tooth recess which is concentrical with respect to the root post, and wherein a sleeve-shaped crown anchor is provided which is adapted to be concentrically secured to the root post and whose lower portion fits into the recess, the crown anchor serves for the attachment of the tooth. Particular features of the embodiments are defined in the dependent claims. Besides the immediately apparent advantages, it will be noted that the construction of the present artificial tooth is simpler and quicker. In addition, a convenient adaptation to the respective case is obtained as the root anchor is adjusted to the size of the artificial tooth to be built and keeping a stock of root anchors of different lengths is no longer necessary.

BRIEF DESCRIPTION OF THE DRAWING

The invention is now explained in more detail by way of embodiments thereof. Hereinafter reference is made to the drawing, wherein FIG. 1 shows a longitudinal cross-section of a tooth stump with a root anchor screwed in;

FIG. 2 shows the same subject as FIG. 1 during milling of the sleeve cavity, the tooth stump being only partially shown in cross-section;

FIG. 3 shows the finished artificial tooth in the same representation as in FIG. 2;

FIG. 4 shows a cross-section in along line IV—IV of FIG. 3; and

FIG. 5 shows a longitudinal cross-section of a tooth stump having a crown anchor according to the prior art.

DESCRIPTION OF THE PREFERRED EMBODIMENT

The following description is based upon the use of the teeth in the lower jaw and may easily be applied to the case of upper jaw. Therefore, if expressions such as "below", "above" and the like are used, their meaning will be reversed in the case of the upper jaw teeth.

FIG. 1 shows a tooth stump 12 in jaw bone 10. A root post 30 is screwed into its root canal 16. Root 30 is provided at its point with a conical tap portion 32 while its shape is otherwise cylindrical except for at least one wedge-shaped longitudinal groove 34 which has the primary purpose of eliminating drilled-out dentine. It is not necessary to produce a matching root bore beforehand.

After screwing root post 30 into root canal 16, a rose cutter 36 (FIG. 2) is applied. The latter is in the form of a sleeve; having internal bore 38 which is cylindrical and fits onto root post 30, which thus acts as a guiding element. Curved cutter 40 is provided at the front of rose cutter 36. At the top, rose cutter 36 terminates in a securing pin 42. The rose cutter will produce a symmetrical recess which is exactly concentrical with respect to root post 30 and has a curved bottom. After retracting rose cutter 36, the root post is shortened to a suitable length, e.g. along separating line 44.

The proper crown anchor 46 can now be fitted onto the free part of root post 30 (FIG. 3). In particular, it serves the purpose of increasing the binding surface with the tooth crown and to improve the binding strength, and it is preferably made of a synthetic material, more particularly a fiber-reinforced composite material. An extremely strong connection with the dentine and the root post is obtained if a hard-enable material is used. Anchor 46 can be cemented, glued, or shrunk in, etc., according to the actual requirements. Due to longitudinal groove 34, into which the material of crown anchor 46 enters (FIG. 4), a rotationally secure arrangement is obtained.

In a last step, possibly after grinding or asymmetrical machining of crown anchor 46, the material of crown 48 is applied (FIG. 3), the crown is shaped, hardened, adjusted (chewing surfaces) and polished. The artificial tooth is thus finished. As usual, the material of the crown is ceramics or a suitable plastics material. It may also be provided with a cap. This last step is known to one skilled in the art.

The object of the invention may be modified or supplemented within the scope of what is defined in the claims. For example, cutting thread 32 of root post 30 may also be a partial thread. The shaft of the root post may have a roughened surface or be provided with a coating which results in a bacteria-tight contact with the dentine. For the tooth recess and thus for rose cutter 36, almost any shape may be chosen. Root post 30 is preferably completely made of titanium, or at least on its external surfaces. It is also usual and sometimes preferred that root post 30 comprises more than one longitudinal groove, e.g. two, three or four. The longitudinal groove or multiple grooves could be extended to the lower end of the cutting thread. This means that a configuration is attained which is known from metal taps or from bone surgery.

In its upper area protruding from the tooth stump, the crown anchor may be provided with recesses, slots 50 and other surface elements 52, e.g. ribs as well, which ensure a rotationally secure and a generally more solid connection. This constitutes a preferred embodiment, and so does an embodiment where crown anchor 46 is upwardly tapered as is indicated in FIG. 3.

I claim:

1. A superstructure for an artificial tooth, comprising:
a root post for being screwed into a root canal of a tooth stump, said root post comprising a cylindrical tap having a cutting thread, said root post being capable of guiding a sleeve-shaped rose cutter having a curved cutting surface for producing a tooth recess having a lower curved portion and which is concentric with respect to said root post; and
a sleeve-shaped crown anchor concentrically secured to said root post and having a lower curved portion which fits into and corresponds with the lower curved portion of said recess, said artificial tooth being secured on said crown anchor.

2. The superstructure for an artificial tooth of claim 1, wherein at least the surfaces of said root post are made of titanium.

3. The superstructure for an artificial tooth of claim 1, wherein said crown anchor is made of a synthetic material, more particularly a fiber reinforced composite material.

4. The superstructure for an artificial tooth of claim 1, wherein said root post is elongated and includes a separating line for shortening said root post, said root post being adapted to be shortened to a length which is shorter than a height of said crown anchor after said root post is screwed into the root canal and after said tooth recess has been drilled.

5. The superstructure for an artificial tooth of claim 4, wherein said crown anchor is conformed such as to be shrunk onto said shortened root post.

6. The superstructure for an artificial tooth of claim 1, wherein a portion of said crown anchor projects above said tooth stump and said crown anchor is upwardly tapered.

7. The superstructure for an artificial tooth of claim 1, wherein said crown anchor has an external surface and connecting means disposed on said external surface for solidly connecting said artificial tooth on said crown anchor.

8. The superstructure for an artificial tooth of claim 7, wherein said connecting means comprises at least one rib disposed on said external surface.

9. The superstructure for an artificial tooth of claim 7, wherein said connecting means comprises at least one slot disposed on said external surface.

10. The superstructure for an artificial tooth of claim 7, further comprising a rose cutter for being guided along said root post for producing a tooth recess as aforesaid.

11. The superstructure for an artificial tooth of claim 1, wherein said root post has at least one groove extending axially along an external side.

12. A method for producing a superstructure for an artificial tooth comprising the steps of:
screwing a root post into a root canal of a tooth stump;
guiding a sleeve-shaped rose cutter over said root post, said rose cutter having a curved cutting surface;
drilling a tooth recess with said rose cutter, said tooth recess being concentric with said root post and having a lower curved portion;
removing the rose cutter;
fitting a sleeve-shaped crown anchor over said root post and into said tooth recess, said crown anchor being concentric with said root post and having a lower curved portion which corresponds with said lower curved portion of said recess; and
securing said artificial tooth on said crown anchor.

13. The method of claim 12, wherein said root post is elongated and further comprising the step of shortening said root post to a length which is shorter than a height of said crown anchor, said root post including a separating line for shortening said root post, after said steps of screwing said root post into the root canal and drilling said tooth recess.

* * * * *